(12) United States Patent
He et al.

(10) Patent No.: US 9,452,062 B2
(45) Date of Patent: Sep. 27, 2016

(54) ADJUSTABLE COMPLEX OF ARTIFICIAL CERVICAL VERTEBRA AND INTERVERTEBRAL CONNECTOR

(75) Inventors: Xijing He, Xi'an (CN); Jie Qin, Xi'an (CN)

(73) Assignee: Xijing He, Xi'an, Shaanxi (CN)

( * ) Notice: Subject to any disclaimer, the term of this patent is extended or adjusted under 35 U.S.C. 154(b) by 82 days.

(21) Appl. No.: 14/129,966

(22) PCT Filed: Jun. 29, 2011

(86) PCT No.: PCT/CN2011/076587
§ 371 (c)(1),
(2), (4) Date: Dec. 28, 2013

(87) PCT Pub. No.: WO2013/000138
PCT Pub. Date: Jan. 3, 2013

(65) Prior Publication Data
US 2014/0194990 A1    Jul. 10, 2014

(51) Int. Cl.
*A61F 2/44* (2006.01)
*A61F 2/30* (2006.01)
*A61F 2/28* (2006.01)

(52) U.S. Cl.
CPC ...... *A61F 2/4465* (2013.01); *A61F 2002/2835* (2013.01); *A61F 2002/304* (2013.01); *A61F 2002/3098* (2013.01); *A61F 2002/30387* (2013.01); *A61F 2002/30392* (2013.01); *A61F 2002/30509* (2013.01); *A61F 2002/30576* (2013.01); *A61F 2002/30578* (2013.01); *A61F 2002/30601* (2013.01); *A61F 2002/30649* (2013.01); *A61F 2002/30785* (2013.01); *A61F 2002/30841* (2013.01); *A61F 2310/00023* (2013.01); *A61F 2310/00796* (2013.01)

(58) Field of Classification Search
CPC .. A61B 2/4425; A61B 2/446; A61B 2/4465; A61B 2002/443
See application file for complete search history.

(56) References Cited

U.S. PATENT DOCUMENTS

2007/0191954 A1\* 8/2007 Hansell et al. ............ 623/17.15
2008/0015704 A1\* 1/2008 Gradl et al. ............... 623/17.16
2012/0101576 A1\* 4/2012 Dewey et al. ............. 623/17.11

\* cited by examiner

*Primary Examiner* — David Bates
*Assistant Examiner* — Olivia C Chang

(57) ABSTRACT

An adjustable complex of an artificial cervical vertebra and an intervertebral connector includes: a vertebra body; and two end plates respectively connected to a top end and a bottom end of the vertebra body by spherical joint structures; wherein the vertebra body comprises: an upper vertebra body; and a lower vertebra body; wherein the upper vertebra body is axially connected to the lower vertebra body by a screw thread; a plurality of radial screw holes are correspondingly provided on side surfaces of the upper vertebra body and the lower vertebra body; a length-fixing screw is provided though the radial screw holes of the upper vertebra body and the lower vertebra body; wherein end plate fixing screws are respectively provided on the two end plates. The adjustable complex has a support function of an artificial vertebra and movability of an artificial intervertebral disc.

3 Claims, 4 Drawing Sheets

ADJUSTABLE COMPLEX OF ARTIFICIAL CERVICAL VERTEBRA AND INTERVERTEBRAL CONNECTOR

CROSS REFERENCE OF RELATED APPLICATION

This is a U.S. National Stage under 35 U.S.C 371 of the International Application PCT/CN2011/076587, filed Jun. 29, 2011.

BACKGROUND OF THE PRESENT INVENTION

1. Field of Invention

The present invention relates to a field of medical prosthesis manufacture, and more particularly to an adjustable complex of an artificial cervical vertebra and an intervertebral connector.

2. Description of Related Arts

Because of the population aging, increasing proportion of desk workers as well as computer users, high traffic accident rate and other factors, patients with cervical vertebra problems such as cervical spondylosis, cervical vertebra fracture and cervical vertebra tumor are increasing. Emphases of surgeries for patients with cervical vertebra problems, especially with cervical spondylosis and cervical vertebra fracture due to the cervical intervertebral disc herniation, are put on: a) reducing pressing, wherein the factors pressing the spinal cord and the nerve root should be eliminated in such a manner that nerve functions can recover faster after the surgery; and b) stabilizing, wherein different types of fusion surgeries are provided and different implant materials (such as autograft bone, allograft bone and artificial vertebra) are utilized for long-term postoperative stabilization. Among the surgeries, the anterior intervertebral disc nucleus pulposus excise with subtotal corpectomy for decompression and intervertebral fusion is currently the most important surgery, and is the surgery with the greatest application advantage. The benefits comprise simple decompression, thorough discectomy and high fusion rate. Anterior intervertebral fusion comprises autograft bone, allograft bone and artificial vertebra grafting fusion. Autograft bone graft has significant osteoinductive, osteoconductive and osteogenesis. Therefore, the surgery has become a gold standard for bone grafting fusion. Advantages of autograft bone grafting fusion are no immunogenicity and fast fusion. However, shortcomings thereof are high postoperative loss rate and secondary damage of harvested bone area (such as donor site bleeding, fracture and infection). The allograft bone graft avoids the above disadvantages, but immunogenicity exists and fusion speed is slow (often takes six months or even more than nine months).

In order to overcome the above disadvantages of autograft and allograft bone graft, postoperative substitute has been looked for. As a result, artificial vertebra was invented. In 1969, Hamdi first reported vertebral tumor excision of patients with waist 2 plasma cell tumor and metastatic adenocarcinoma, and replaced the pathological vertebra with prosthesis (Hamdi, F A. *Prosthesis for an excised lumbar vertebra: a preliminary report*. Can Med Assoc J, 1969, 100, 12: 576-80.). According to the materials, the artificial vertebra can be classified into artificial vertebra made by metal materials, artificial vertebra made by new composite materials and artificial vertebra made by other materials. According to the structure and function, the artificial vertebra can be classified into pure supporting type, bracing and fixing type and adjustable fixing type. The pure supporting type artificial vertebra is mainly mounted on an upper vertebra and a lower vertebra by injecting bone cement for filling the bone defeat caused by vertebra excision. The fixing effect thereof is poor. The bracing and fixing type artificial vertebra is mainly mounted on an upper vertebra and a lower vertebra by spikes for instantly stabilizing the vertebra. Titanium mesh is the most commonly used artificial vertebra for bracing and fixing and is widely used in the reconstruction of the vertebra. However, length of the titanium mesh is fixed and is nonadjustable. Therefore, the choice of the vertebra is very strict, otherwise it is difficult to restore the ideal vertebral height. Besides, risk of falling exists. Different adjustable fixing type artificial vertebras with a variety of characteristics have been developed by scholars in the world. And the artificial vertebras have achieved a certain effect in clinical application. For example, the Synex artificial vertebra has a titanium hollowed mesh structure and a length thereof is adjustable. Knop and other people utilized the Synex artificial vertebra for the reconstruction of the anterior injury of thoracic and lumbar vertebra for providing sufficient 3-dimensional stability of the vertebra. However, after length adjustment, posterior implant of the Synex artificial vertebra is difficult and technical requirement is high. Therefore, the anterior or combined posteroanterior surgery has a serious trauma and takes a long time (Knop, Christian; Lange, Uta; Reinhold, Maximilian; Blauth, Michael. *Vertebral body replacement with Synex in combined posteroanterior surgery for treatment of thoracolumbar injuries*. Oper Orthop Traumatol. 2005, 17 (3): 249-80.). Zhao Dinglin (Zhaoding Lin, Chen De, Zhao Jie, et al. *Research and clinical applications of adjustable hollowed artificial vertebra*. Chinese Journal of Orthopaedics, 2001, 21:222-224.) has developed a hollowed adjustable titanium alloy artificial vertebra. A length thereof is adjustable for ideally recovering vertebral height. Because of a hollowed structure, bone graft is able to be provided therein in such a manner that prosthesis is permanently fused with the vertebra. However, only spikes contact with the upper and lower vertebras for mounting and the prosthesis is rigidly mounted. Therefore, the internal bone graft has problems of stress shielding and bone resorption.

The shapes and materials of the artificial vertebras are adjusted and improved for simplifying the surgical steps, reducing surgical trauma, realizing instant postoperative stabilization, and fastening fusion. However, the above artificial vertebras have the same problem that the operated vertebras will completely lose original movability after the surgery, which is considered to accelerate postoperative cervical degenerative disease, lead to cervical intervertebral disc herniation of the adjacent vertebras, and cause vertebral bone hyperplasia, etc. Long-term follow-up results illustrated that after the anterior cervical vertebra fusion surgery, up to 92% of patients had adjacent segment degeneration, although the clinical symptoms are not consistent with the severity of the X line (Goffin, Jan, Geusens, Eric, Vantomme, Nicolaas, et al. *Long-term follow-up after interbody fusion of the cervical spine*. J Spinal Disord Tech, 2004, 17(2): 79-85.). Hilibrand and the others found that after anterior fusion surgery, clinical symptoms related to adjacent segment degeneration occur to about 2.9% of patients each year. Furthermore, the statistical results illustrate that clinical symptoms caused by adjacent segment degeneration will occur to 25.6% of patients in 10 years (Hilibrand A S, Carlson G D, Palumbo M A, et al. *Radiculopathy and myelopathy at segments adjacent to the site of a previous anterior cervical arthrodesis* [J]. J Bone Joint Surg Am, 1999, 81 (4): 519-528.). The biomechanical experimental results also confirmed that pressure inside the intervertebral disc of the adjacent segments is increased after the fusion surgery. Kinematic iconography evidence also illustrated that relative movability of adjacent segment vertebras is increased after the fusion surgery. The above factors are very likely to accelerate the postoperative adjacent segment degeneration.

For overcoming the loss of movability of the operated segment, adjacent segment degeneration and other shortcomings, scientists and doctors in the world have established a non-fusion vertebral surgery method whose philosophy is motion preservation. The artificial intervertebral disc replacement surgery (also known as intervertebral disc arthroplasty) is a typical non-fusion surgery. Intervertebral disc prostheses such as Bryan prosthesis, ProDisc-C prosthesis, Prestige prosthesis and PCM prosthesis are mainly utilized for clinical application. Currently, best indications for artificial disc replacement surgery are single segment and physiological cervical curvature (Sekhon L H. *Cervical arthroplasty in the management of spondylotic myelopathy* [J]. J SpinalDisord Tech, 2003, 16 (4): 307-313). Recognized contraindications are osteoporosis and intervertebral instability (Wiffield C C, Skrzyp iec D, Jackowski A, et al. *Internal stress distribution in cervical intervertebral discs: the influence of an artificial cervical joint and simulated anterior interbody fusion* [J ]. J Spinal Disord Tech, 2003, 16 (5): 441-449.). Although artificial intervertebral discs have different materials and shapes, the common disadvantages are as follows: first, only single replacement of intervertebral disc is able to be provided and the combined vertebral lesions (such as vertebral tumors and surgeries needing vertebral decompression) cannot be treated. Second, most scholars do not agree to multi-segment intervertebral disc replacement, especially the replacement of adjacent intervertebral discs at the same time.

In summary, the conventional technology is not able to solve the problem of movability after cervical vertebra surgery, especially the problem of no movability after multi-segment surgery and the adjacent segment degeneration after fusion surgery.

Accordingly, an adjustable complex of an artificial cervical vertebra and an intervertebral connector with support function like the artificial vertebra and movability like the artificial intervertebral disc is developed according to the present invention.

SUMMARY OF THE PRESENT INVENTION

An object of the present invention is to overcoming the above shortcomings and to provide an adjustable complex of an artificial cervical vertebra and an intervertebral connector, wherein the adjustable complex has a support function of an artificial vertebra and movability of an artificial intervertebral disc; a length thereof is adjustable for instantly stabilizing after an anterior cervical vertebra surgery and supporting; the adjustable complex is also able to realize preoperative movability reconstruction for simulating movability and normal vertebral length.

Accordingly, in order to accomplish the above object, the present invention provides an adjustable complex of an artificial cervical vertebra and an intervertebral connector, comprising:

a vertebra body; and two end plates respectively connected to a top end and a bottom end of the vertebra body by spherical joint structures;

wherein the vertebra body comprises:

an upper vertebra body; and a lower vertebra body;

wherein the upper vertebra body is axially connected to the lower vertebra body by a screw thread; a plurality of radial screw holes are correspondingly provided on side surfaces of the upper vertebra body and the lower vertebra body; a length-fixing screw is provided though the radial screw holes of the upper vertebra body and the lower vertebra body;

wherein end plate fixing screws are respectively provided on the two end plates.

Preferably, the spherical joint structure comprises:

a joint ball structure mounted on the end plate; and an acetabulum structure corresponding to the joint ball structure and mounted on an end of the upper vertebra body or the lower vertebra body, wherein an inner space of the acetabulum structure has a cylindrical space at a center thereof and two hemispherical spaces intersecting the cylindrical space; the inner space of the acetabulum structure is big and an opening thereof is small for containing the joint ball structure.

Preferably, the end plate comprises:

a disc, wherein the joint ball structure is vertically mounted on an internal surface of the disc, two the end plate fixing screws are mounted on an external surface of the disc at an edge far away from the joint ball structure by two adjacent screw holes; a predetermined angel is provided between an axial direction of the end plate fixing screw and a plane of the disc.

Preferably, the external surface of the disc has a matting-like rough structure, and is coated by a biological hydroxyapatite layer.

Preferably, a thickness of the hydroxyapatite layer is 1 μm, a toothed structure with a size of 1 μm is provided on a rear portion of the external surface of the disc.

Preferably, the disc is thinner at which the end plate fixing screw is mounted on and thicker at which the joint ball structure is mounted on; the disc has a sliced surface when observed from a side, the sliced surface extends from a center line of the disc to a bottom front for forming the sliced surface with an angle of 10°, in such a manner that the end plate forms an inclined surface with an angle of 80° with adjacent the upper vertebra body and forms an inclined surface with an angle of 100° with adjacent the lower vertebra body.

Preferably, an external screw thread is provided on a down neck of the upper vertebra body, a barrel structure with an internal screw thread is provided on a top portion of the lower vertebra body; the down neck of the upper vertebra body is screwed into the internal screw thread of the lower vertebra body through the external screw thread; a plurality of radial screw through-holes are evenly distributed on the upper vertebra body and the lower vertebra body in an axial direction, the length-fixing screw is screwed into the radial screw through-holes for fixing a relative axial position of the upper vertebra body and the lower vertebra body.

Preferably, a minimum length of the adjustable complex is 23 mm, a maximum length thereof is 29 mm, an adjustable range is 6 mm.

Preferably, a front end of the end plate fixing screw is a pointed end, a rear end of the end plate fixing screw is a nut; a portion close to the nut is slightly thicker than a portion close to the pointed end.

Therefore, advantages of the present invention are as follows:

The present invention is able to provide instant support after an anterior cervical vertebra surgery and replace movability of a normal cervical vertebra by an intervertebral connector thereof for effectively preventing degeneration of adjacent segments caused by a fusion surgery. In addition, with bone graft and the hydroxyapatite layer of the complex, biological fusion and long-term stabilization are realized. The surgery is not difficult, trauma is small, and thus promotion is easy. Because the length of the complex is adjustable, production and carrying burdens are decreased for suiting vast majority of the population.

These and other objectives, features, and advantages of the present invention will become apparent from the following detailed description, the accompanying drawings, and the appended claims.

Figure 1:
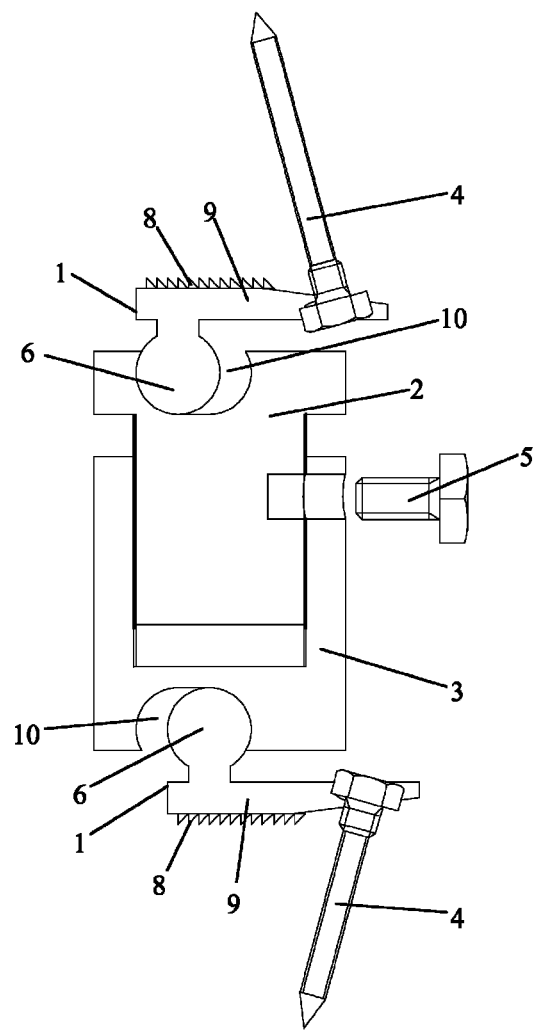
FIG. 1 is a perspective view of an adjustable complex of an artificial cervical vertebra and an intervertebral connector according to a preferred embodiment of the present invention.

Reference numbers of elements: 1—end plate, 2—upper vertebra body, 3—lower vertebra body, 4—end plate fixing plate, 5—length-fixing plate, 6—joint ball structure, 7—screw hole, 8—toothed structure, 9—disc, 10—acetabulum structure.

DETAILED DESCRIPTION OF THE PREFERRED EMBODIMENT

Referring to the drawings, the present invention is further illustrated.

Referring to FIG. 1 of the drawings, an adjustable complex of an artificial cervical vertebra and an intervertebral connector is illustrated, comprising:

a vertebra body; and two end plates 1 respectively connected to a top end and a bottom end of the vertebra body by spherical joint structures;

wherein the vertebra body comprises:

an upper vertebra body 2; and a lower vertebra body 3;

wherein the upper vertebra body 2 is axially connected to the lower vertebra body 3 by a screw thread; a plurality of radial screw holes are correspondingly provided on side surfaces of the upper vertebra body 2 and the lower vertebra body 3; a length-fixing screw 5 is provided though the radial screw holes of the upper vertebra body 2 and the lower vertebra body 3;

wherein end plate fixing screws 4 are respectively provided on the two end plates.

Referring to FIGS. 1-2 and FIGS. 4-5 of the drawings, the spherical joint structure is illustrated, comprising:

a joint ball structure 6 mounted on the end plate 1; and an acetabulum structure 10 corresponding to the joint ball structure 6 and mounted on an end of the upper vertebra body 2 or the lower vertebra body 3, wherein an inner space of the acetabulum structure 10 comprises a cylindrical space at a center thereof and two hemispherical spaces intersecting the cylindrical space; the inner space of the acetabulum structure 10 is big and an opening thereof is small for containing the joint ball structure 6; the joint ball structure 6 is corresponding to the acetabulum structure 10 for providing a movability with four degrees of freedom of the intervertebral connector.

Preferably, the structure of the joint ball structure 6 is formed by 85% of a sphere with a diameter of 4 mm and a cylindrical structure. The joint ball structure 6 is matching with the acetabulum structure 10 of the upper vertebra body or the lower vertebra body. A right portion and a left portion of the acetabulum structure 10 are completely matching with the joint ball structure 6 (which means diameters thereof are also 4 mm). The acetabulum structure 10 is formed by stretching a sphere with a diameter of 4 mm by 1.5 mm along an X-axis (which is a horizontal line connecting midpoints of a front edge and a rear edge of the vertebra body). 3-dimensionally, the acetabulum structure 10 is 85% of a nest column structure formed by a hemisphere with a diameter of 4 mm, a cylinder with a basal diameter of 4 mm and a height of 1.5 mm and a hemisphere with a diameter of 4 mm. Therefore, the intervertebral connector has advantages as follows: a) a fitness of 85% is able to form more than half of the joint anastomosis, which guarantees absolute stability of the intervertebral connector and does not lead to postoperative dislocation; b) a action center of the intervertebral connector is at a slightly rearward position of a vertebral column, which is at a movement axis of a normal vertebra and has little effects on biomechanical properties of the vertebra after the implantation; c) the intervertebral connector is able to provide activities with four degrees of freedom, (wherein the X-axis is defined by the horizontal line connecting midpoints of the front edge and the rear edge of the vertebra body, a Y-axis is defined by a horizontal line connecting midpoints of a right edge and a left edge of the vertebra body, and a Z-axis is defined by a vertical line); respectively, the four degrees of freedom are forward and backward flexion with about 15° (by rotating around the Y-axis), leftward and rightward flexion with about 15° (by rotating around the X-axis), clockwise and anticlockwise rotation limited by a vertebral posterior column with 15° to 20° (by rotating around the Z-axis), and forward and backward translation with about 1.5 mm (by translating along the X-axis). It is the most important that the intervertebral connector is able to realize the forward and backward translation which is impossible for almost all the artificial intervertebral disks and the artificial vertebras. Most of the literatures have confirmed that the human vertebra is able to provide forward and backward flexion, leftward and rightward flexion, clockwise and anticlockwise rotation, as well as forward and backward translation of an upper vertebra body and a lower vertebra body, wherein the translation has a positive effect on preventing the intervertebral disc and the cervical vertebra from degeneration. However, a distance of the translation should not be too long. If the distance is too long, vertebral instability will be caused. Therefore, intervertebral connector formed by the uniquely designed nest column structure is able to provide the forward and backward translation with about 1.5 mm of the upper vertebra body and the lower vertebra body, in such a manner that human cervical vertebra simulation is maximized and postoperative degeneration of the cervical diseases is inhibited.

Figure 5:
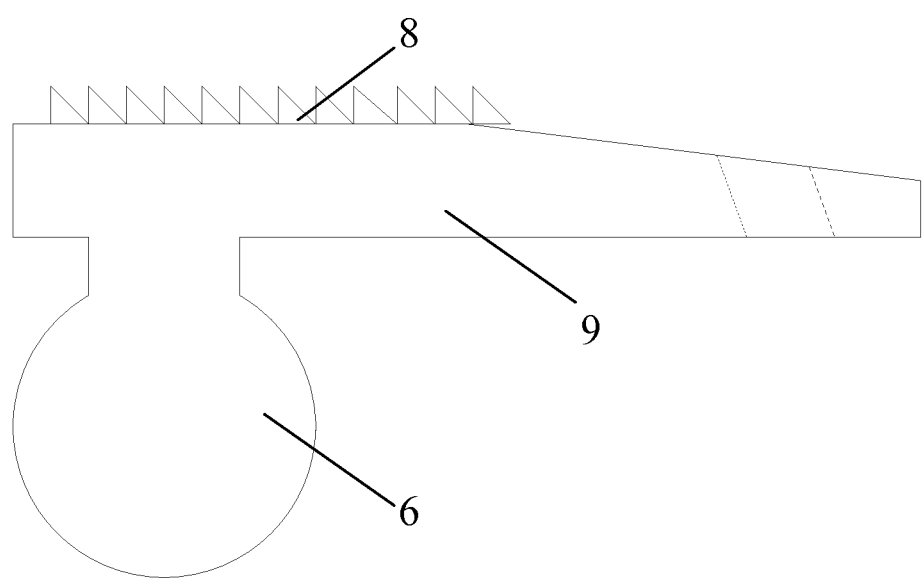
FIG. 5 is a left view of an end plate according to the preferred embodiment of the present invention.
Figure 6:
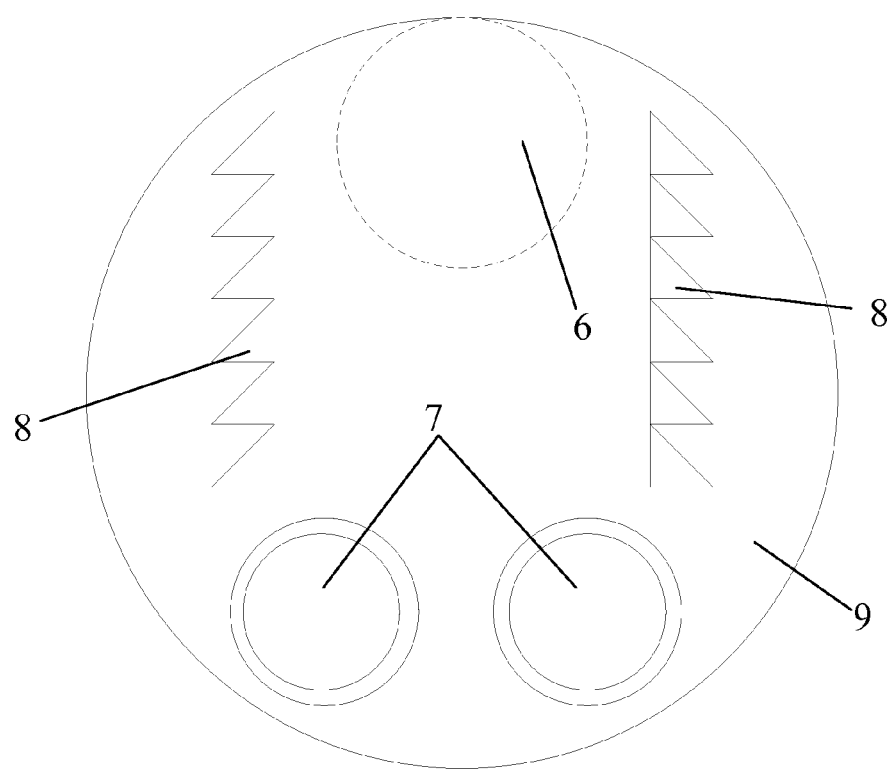
FIG. 6 is a top view of the end plate according to the preferred embodiment of the present invention.

Referring to FIG. 5-6 of the drawings, the end plate 1 is illustrated, comprising:

a disc 9, wherein the joint ball structure 6 is vertically mounted on an internal surface of the disc 9, two the end plate fixing screws 4 are mounted on an external surface of the disc 9 at an edge far away from the joint ball structure 6 by two adjacent screw holes 7; a predetermined angel is provided between an axial direction of the end plate fixing screw 4 and a plane of the disc 9 (as illustrated in the FIG. 1). The disc 9 is thinner at which the end plate fixing screw 4 is mounted on and thicker at which the joint ball structure 6 is mounted on. The external surface of the disc 9 has a toothed structure 8.

Preferably, the disc 9 of the end plate 1 is thinner at a front part and thicker at a rear part; the disc 9 has a sliced surface with a angle of about 10° when observed from a side, the sliced surface extends from a center line of the disc 9 to a bottom front for forming the sliced surface with an angle of about 10°, in such a manner that the end plate 1 forms an inclined surface with an angle of 80° with adjacent the upper vertebra body and forms an inclined surface with an angle of 100° with adjacent the lower vertebra body. The two inclined surfaces are very conducive to that the operated vertebra closely fits the end plates the adjacent upper vertebra and the adjacent lower vertebra. Two screw holes 7 are provided at the front part of the disc 9, (screw hole positions are illustrated in the FIG. 6, a directions of the screw holes are 20° from a front edge of the adjacent vertebra body), the two screw holes have internal screw threads for cooperating with the end plate fixing screws 4. A front end of the end plate fixing screw 4 is a pointed end, a rear end of the end plate fixing screw 4 is a nut (as illustrated in the FIG. 1). A portion close to the nut is slightly thicker than a portion close to the pointed end. The end plate fixing screw 4 is implanted into the vertebra body adjacent to the operated vertebra with an angle of 20°. The nut of the end plate fixing screw 4 cooperates with the screw holes 7. Because the internal screw thread of the screw hole 7 cooperates with the long end plate fixing screw 4, the complex is stably mounted on the vertebra body adjacent to the operated vertebra for instantly stabilizing and supporting. Meanwhile, compared to front screw fixing, the end plate fixing screw 4 according to the above fixing method screws deeper and is more consistent with the biomechanical properties. In addition, a reason why the end plate fixing screw 4 is thinner at the front end and thicker at the rare end corresponding to the screw hole 7 according to the present invention, is that with the above structure, an angle of the end plate fixing screw 4 is easy to be adjusted when being inserted through the screw hole 7. After the end plate fixing screw 4 is screwed into the adjacent vertebra body, the nut end cooperates with the thread of the screw holes 7 for locking the angle of the end plate fixing screw 4.

Preferably, the external surface of the disc 9 has a matting-like rough structure, and is coated by a biological hydroxyapatite layer treated by a plasma oxidation technology. A thickness of the hydroxyapatite layer is 1 μm, a toothed structure 8 with a size of 1 μm is provided on a rear portion of the external surface of the disc 9. All the external surface treatments are able to accelerate an early stage fusion of the end plate and the adjacent vertebra body and are conducive to biological fusion and long-term stability.

Figure 2:
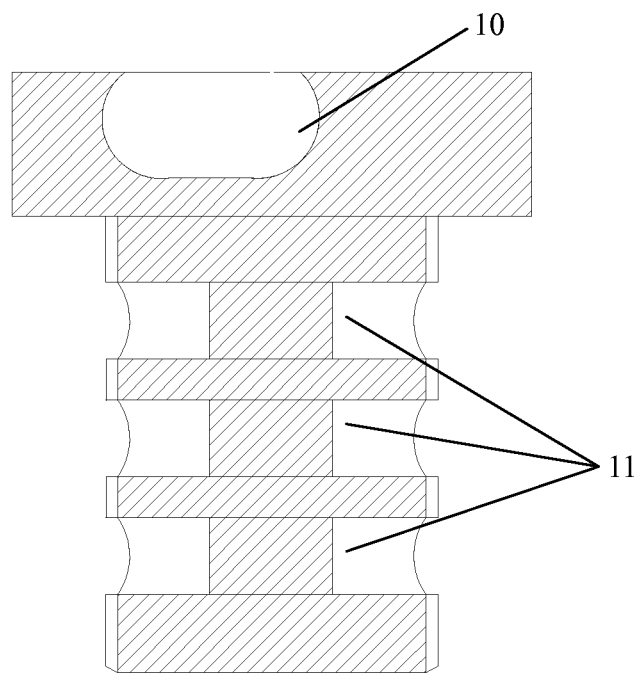
FIG. 2 is a sectional view of an upper vertebra body according to the preferred embodiment of the present invention.
Figure 3:
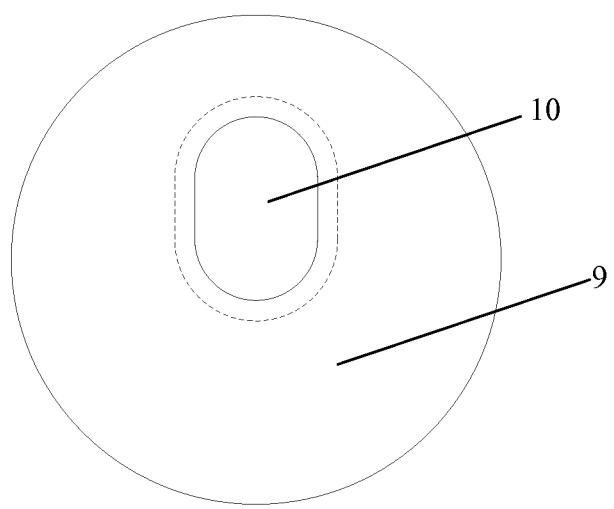
FIG. 3 is a top view of the upper vertebra body according to the preferred embodiment of the present invention.
Figure 4:
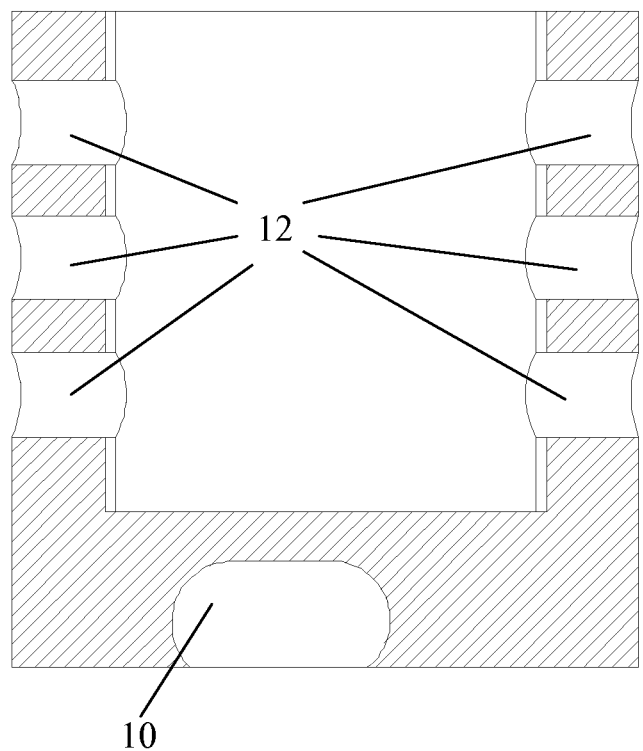
FIG. 4 is a sectional view of a lower vertebra body according to the preferred embodiment of the present invention.

Referring to the FIG. 1 or the FIG. 2 and the FIG. 4, an external screw thread is provided on a down neck of the upper vertebra body 2, a barrel structure with an internal screw thread is provided on a top portion of the lower vertebra body 3; the down neck of the upper vertebra body 2 is screwed into the internal screw thread of the lower vertebra body 3 through the external screw thread; a plurality of radial screw through-holes 11 and 12 (three radial screw through-holes 11 and 12 are illustrated in the FIGS. 2-3) are evenly distributed on the upper vertebra body 2 and the lower vertebra body 3 in an axial direction, the length-fixing screw 5 is screwed into the radial screw through-holes for fixing a relative axial position of the upper vertebra body 2 and the lower vertebra body 3.

Preferably, The lower vertebra body 3 comprises an upper hollow cylindrical structure (with a diameter of about 12 mm, a height of about 10 mm, and a wall thickness of about 2 mm) and a lower solid cylindrical portion (with a diameter of about 12 mm, a height of about 4 mm) (as illustrated in the FIG. 4). A fixing hole with a diameter of 2 mm is provided in front of the upper hollow cylindrical structure, wherein the fixing hole has an internal thread. Four consecutive fusion holes with a diameter 2 mm are provided on a left side and a right side thereof, wherein the fusion holes have no thread. An external surface of the lower vertebra body 3 is coated by a 1 μm-thick biological hydroxyapatite layer treated by the plasma oxidation technology. The acetabulum structure 10 is provided at a bottom center of the lower vertebra body 3, wherein dotted lines below illustrates a position of the acetabulum structure 10, the acetabulum structure 10 is marching with the joint ball structure 6 of the end plate 1.

Preferably, the external thread on the lower portion of the upper vertebra body 2 is marching with the internal thread on the upper portion of the lower vertebra body 3. Because a pitch is 1 mm, rotating outwardly by 1 circle will increase the length of the entire complex by 1 mm. Four fusion screw holes 12 are respectively provided on a left side and a right side of the lower portion of the upper vertebra body 2. Four fusion screw holes 11 are respectively provided on a left side and a right side of the upper portion of the lower vertebra body 3. A diameter of the fusion screw holes are 2 mm. The fusion screw hole has no thread. The fusion screw hole of the upper vertebra body 2 (the screw hole 12) will coincide with some of the fusion screw hole of the lower vertebra body 3 (the screw hole 11) by rotating the upper vertebra body 2 inwardly by two circles. After the long-term implantation, crushed bones in the lower hollow cylindrical structure of the upper vertebra body 2 will grow along the fusion screw holes for stable fusion of the stable vertebra body and the operated vertebra. In addition, the hydroxyapatite layer coated on the upper vertebra body 2 and the lower vertebra body 3 is able to accelerate the postoperative fusion, realize biological fusion, and ensure long-term stability.

Preferably, four adjusting screw hole 11 provided on a bottom front of the upper vertebra body 2 and a fixing screw hole provided in front of the lower vertebra body 3 have internal threads for matching with the length-fixing screw 5. Because diameters of the adjusting screw holes and the fixing screw hole are all 2 mm, the fixing screw hole of the lower vertebra body 3 will coincide with the adjusting screw holes of the upper vertebra body 2 by rotating the upper vertebra body 2 inwardly by two circles. At this time, the length-fixing screw 5 can be screwed through the fixing screw hole and the adjusting screw hole for fixing the length of the complex by anastomosis of the lower internal thread of the upper vertebra body 2 and the upper internal thread of the lower vertebra body 3 and a holding force of the screw 5, the fixing screw hole and the adjust t screw holes. The four adjustment screw holes ensure that an adjustable range of the length of the entire complex is 6 mm, which satisfies a length requirement of normal cervical vertebra.

The above vertebra body 2 cooperates with the lower vertebra body 3, and the length of the entire complex can be adjusted by rotating (wherein a minimum length of the adjustable complex is 23 mm, a maximum length thereof is 29 mm; an adjustable range is 6 mm).

In summary, the adjustable complex of the artificial cervical vertebra and the intervertebral connector according to the present invention is especially suitable for cervical spondylosis caused by intervertebral disc herniation. The adjustable complex is also suitable for intervertebral disk excision, subtotal corpectomy and replacement surgery with the adjustable complex. Meanwhile, for the single cervical vertebra tumor, subtotal corpectomy and replacement surgery with the adjustable complex is able to be applied. In addition, the adjustable complex is suitable for the patients on whom the artificial cervical intervertebral disk replacement is not able to be applied, postoperative renovation of the artificial cervical intervertebral disk replacement, serious postoperative degeneration of the cervical vertebra fusion, etc. Referring to the intervertebral disk excision, the subtotal corpectomy and the replacement surgery with the adjustable complex, an application example of the present invention in a surgery is illustrated for a patient with indication while no contraindication is detected. Routine preoperative preparation is usually provided with tracheal intubation general anesthesia. Dorsal decubitus is utilized, a soft pillow is padded under both shoulders, head naturally extends backwards, a soft head ring is padded under a back of the head for avoiding pressing wounds, and small sandbags are respectively placed at both sides of the head for preventing the head from rotating during the surgery. An incision is generally a transverse incision at a front portion of neck for exposing diseased vertebra and intervertebral disc. Positioning is provided by a C-arm X-ray machine during the surgery. Spreading screws are screwed into centers of upper and lower vertebra bodies of the vertebra body to be processed with subtotal corpectomy. A spreader is cased on the spreading screws for spreading the upper and lower vertebra bodies. With respect to decompression, annulus fibrosus of the upper and lower intervertebral disks of the vertebra body to be operated on are cut with a sharp knife. The intervertebral disc tissues are removed by nucleus pulposus pliers. Front cortical bones and cancellous bones are removed by a nipper rongeur with three joints until nearly reaching the posterior edge of vertebra. Then the intervertebral disks are completely removed and repairing articular surfaces with a curette, a rongeur and a round filing until subchondral bleeding in such a manner that the end plates are substantially parallel to each other, wherein the bony end plate should not be destroyed. A gap between the posterior edge of vertebra body and the posterior longitudinal ligament is isolated by a nerve stripper. Cortical bones of the posterior edge is gradually removed by a gun-type rongeur for forming a rectangle decompression slot (wherein the posterior longitudinal ligament may need to be cut according to requirements), a width of the rectangle decompression slot is approximately 12 mm. A height of the anterior cervical column is back to normal by adjusting the height of the spreader. At the same time, the excised vertebral bone is crashed into bone fragments with a size of about 2 mm for filling the lower hollow cylindrical structure of the upper vertebra body. Then the complex is implanted and the length thereof is adjusted to a desired height in such a manner that the upper end plate of the lower vertebra body is matching with the lower end plate of the upper vertebra body. According to the above length, the length-fixing screw 5 is screwed in for fixing the length of the complex. The upper and lower vertebra bodies of the complex are hit into the decompression slot. The upper end plate of the lower vertebra body and the lower end plate of the upper vertebra body are drilled according the screw holes 7 on the end plates and the end plate fixing screws 4 are screwed into the upper and lower vertebra bodies with an angle of 20°. Then the spreader is release in such a manner that the complex is embedded tightly. After examined by the C-arm X-ray machine, the wound is washed, drainage is prevented, and the wound is sutured layer by layer. A cervical gear is utilized for 40 days after the surgery for preventing the neck from moving. Antibiotics are preventively utilized. The patient should be closely observed. Other things are the same as the conventional anterior cervical surgery.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An adjustable complex of an artificial cervical vertebra and an intervertebral connector, comprising:
   an artificial vertebra body; and
   two end plates respectively connected to a top end and a bottom end of said artificial vertebra body by spherical joint structures;
   wherein said artificial vertebra body comprises:
   an upper artificial vertebra body; and
   a lower artificial vertebra body;
   wherein said upper artificial vertebra body is axially connected to said lower artificial vertebra body; a plurality of radial screw holes are correspondingly provided on side surfaces of said upper artificial vertebra body and said lower artificial vertebra body; a length-fixing screw is provided though said radial screw holes of said upper artificial vertebra body and said lower artificial vertebra body;
   wherein end plate fixing screws are respectively provided on said two end plates
   wherein said spherical joint structure comprises:
   a joint ball structure mounted on each of said two end plates; and
   a socket structure corresponding to said joint ball structure and mounted on an end of said upper artificial vertebra body or said lower artificial vertebra body, wherein an inner space of said socket structure is a capsule-shaped space formed by a cylindrical space at a center thereof and two hemispherical spaces intersecting said cylindrical space; said inner space of said socket structure has a diameter larger than that of a surface opening for containing said joint ball structure; wherein said joint ball structure provides both translational and rotary motions inside said inner space;
   wherein each of said two end plates comprises:
   a disc, wherein said joint ball structure is vertically mounted on an internal surface of said disc at a distal end, two said end plate fixing screws are mounted on an external surface of said disc at a proximal end by two adjacent screw holes; a predetermined angle is provided between an axial direction of each of said two end plate fixing screws and a plane of said disc;

wherein said disc is thinner at the proximal end which each of said two end plate fixing screws is mounted on and thicker at the distal end which said joint ball structure is mounted on; said disc has a sliced surface when observed from a side, said sliced surface extends from a center line of said disc toward a proximal portion for forming said sliced surface with an angle of 10°, in such a manner that each of said two end plates forms an inclined surface with an angle of 80° with adjacent said upper artificial vertebra body and forms an inclined surface with an angle of 100° with adjacent said lower artificial vertebra body.

2. An adjustable complex of an artificial cervical vertebra and an intervertebral connector, comprising:

an artificial vertebra body; and two end plates respectively connected to a top end and a bottom end of said artificial vertebra body by spherical joint structures;

wherein said artificial vertebra body comprises:

an upper artificial vertebra body; and a lower artificial vertebra body;

wherein said upper artificial vertebra body is axially connected to said lower artificial vertebra body; a plurality of radial screw holes are correspondingly provided on side surfaces of said upper artificial vertebra body and said lower artificial vertebra body; a length-fixing screw is provided though said radial screw holes of said upper artificial vertebra body and said lower artificial vertebra body;

wherein end plate fixing screws are respectively provided on said two end plates wherein said spherical joint structure comprises:

a joint ball structure mounted on each of said two end plates; and a socket structure corresponding to said joint ball structure and mounted on an end of said upper artificial vertebra body or said lower artificial vertebra body, wherein an inner space of said socket structure is a capsule-shaped space formed by a cylindrical space at a center thereof and two hemispherical spaces intersecting said cylindrical space; said inner space of said socket structure has a diameter larger than that of a surface opening for containing said joint ball structure; wherein said joint ball structure provides both translational and rotary motions inside said inner space;

wherein each of said two end plates comprises:

a disc, wherein said joint ball structure is vertically mounted on an internal surface of said disc at a distal end, two said end plate fixing screws are mounted on an external surface of said disc at a proximal end by two adjacent screw holes; a predetermined angle is provided between an axial direction of each of said two end plate fixing screws and a plane of said disc;

wherein said external surface of said disc has a matting-like rough structure, and is coated by a biological hydroxyapatite layer;

wherein said disc is thinner at the proximal end which each of said two end plate fixing screws is mounted on and thicker at the distal end which said joint ball structure is mounted on; said disc has a sliced surface when observed from a side, said sliced surface extends from a center line of said disc toward a proximal for forming said sliced surface with an angle of 10°, in such a manner that each of said two end plates forms an inclined surface with an angle of 80° with adjacent said upper artificial vertebra body and forms an inclined surface with an angle of 100° with adjacent said lower artificial vertebra body.

3. An adjustable complex of an artificial cervical vertebra and an intervertebral connector, comprising:

an artificial vertebra body; and two end plates respectively connected to a top end and a bottom end of said artificial vertebra body by spherical joint structures;

wherein said artificial vertebra body comprises:

an upper artificial vertebra body; and a lower artificial vertebra body;

wherein said upper artificial vertebra body is axially connected to said lower artificial vertebra body; a plurality of radial screw holes are correspondingly provided on side surfaces of said upper artificial vertebra body and said lower artificial vertebra body; a length-fixing screw is provided though said radial screw holes of said upper artificial vertebra body and said lower artificial vertebra body;

wherein end plate fixing screws are respectively provided on said two end plates wherein said spherical joint structure comprises:

a joint ball structure mounted on each of said two end plates; and a socket structure corresponding to said joint ball structure and mounted on an end of said upper artificial vertebra body or said lower artificial vertebra body, wherein an inner space of said socket structure is a capsule-shaped space formed by a cylindrical space at a center thereof and two hemispherical spaces intersecting said cylindrical space; said inner space of said socket structure has a diameter larger than that of a surface opening for containing said joint ball structure; wherein said joint ball structure provides both translational and rotary motions inside said inner space;

wherein each of said two end plates comprises:

a disc, wherein said joint ball structure is vertically mounted on an internal surface of said disc at a distal end, two said end plate fixing screws are mounted on an external surface of said disc at a proximal end by two adjacent screw holes; a predetermined angle is provided between an axial direction of each of said two end plate fixing screws and a plane of said disc;

wherein said external surface of said disc has a matting-like rough structure, and is coated by a biological hydroxyapatite layer;

wherein a thickness of said hydroxyapatite layer is 1 µm, a toothed structure with a size of 1 µm is provided on a distal portion of said external surface of said disc;

wherein said disc is thinner at the proximal end which each of said two end plate fixing screws is mounted on and thicker at the distal end which said joint ball structure is mounted on; said disc has a sliced surface when observed from a side, said sliced surface extends from a center line of said disc toward a proximal for forming said sliced surface with an angle of 10°, in such a manner that each of said two end plates forms an inclined surface with an angle of 80° with adjacent said upper artificial vertebra body and forms an inclined surface with an angle of 100° with adjacent said lower artificial vertebra body.

* * * * *